US005693317A

United States Patent [19]

Reich et al.

[11] Patent Number: 5,693,317
[45] Date of Patent: Dec. 2, 1997

[54] CONDITIONING RINSE COMPOSITIONS WHICH FACILITATES SETTING OF HAIR

[75] Inventors: Charles Reich, Highland Park; Donna A. Hartnett, Dayton; Clarence R. Robbins, Martinsville; Kurt T. Sackariasen, Point Pleasant Beach; Amrit M. Patel, Dayton, all of N.J.

[73] Assignee: Colgate-Palmolive Company, New York, N.Y.

[21] Appl. No.: 464,201

[22] Filed: Jun. 5, 1995

Related U.S. Application Data

[62] Division of Ser. No. 268,993, Jun. 30, 1994, which is a continuation of Ser. No. 49,194, Apr. 19, 1993, abandoned, which is a continuation-in-part of Ser. No. 822,377, Jan. 17, 1992, abandoned, which is a continuation-in-part of Ser. No. 768,144, Sep. 30, 1991, abandoned.

[51] Int. Cl.$^6$ .............................. A61K 7/07; A61K 7/08
[52] U.S. Cl. .................. 424/70.15; 424/70.17; 424/78.03; 514/938; 514/939; 252/304
[58] Field of Search .......................... 424/70.11, 70.15, 424/70.17, 78.03; 514/938, 939

[56] References Cited

U.S. PATENT DOCUMENTS

| | | | |
|---|---|---|---|
| 3,907,984 | 9/1975 | Calvert et al. | 424/47 |
| 3,927,199 | 12/1975 | Michelli | 424/47 |
| 4,196,190 | 4/1980 | Gehman et al. | 4224/47 |
| 4,348,380 | 9/1982 | Jacquet et al. | 424/47 |
| 4,543,249 | 9/1985 | Nelson | 424/70 |
| 4,673,571 | 6/1987 | Mahieu et al. | 424/70 |
| 4,711,776 | 12/1987 | Suzuki et al. | 424/70 |
| 4,777,037 | 10/1988 | Wagman et al. | 424/70 |
| 4,898,725 | 2/1990 | Hoeffkes et al. | 424/70 |
| 4,902,499 | 2/1990 | Bolich, Jr. et al. | 424/70 |
| 4,963,348 | 10/1990 | Bolich | 424/71 |
| 5,019,377 | 5/1991 | Torgerson | 424/70 |
| 5,034,218 | 7/1991 | Duvel | 424/70 |
| 5,120,531 | 6/1992 | Wells | 424/70 |
| 5,160,730 | 11/1992 | Dubief et al. | 424/59 |

FOREIGN PATENT DOCUMENTS

| | | | |
|---|---|---|---|
| 0130609 | 1/1985 | European Pat. Off. | C11D 1/66 |
| 0138395 | 4/1985 | European Pat. Off. | A61K 7/075 |
| 0274086 | 7/1988 | European Pat. Off. | A61K 7/11 |
| 0424260 A1 | 2/1991 | European Pat. Off. | |
| 0539251 | 4/1993 | European Pat. Off. | |
| 3503618 | 2/1985 | Germany | A61K 7/06 |
| 5403522287 | 3/1979 | Japan . | |
| 56169614 | of 1981 | Japan . | |
| 2206045 | 12/1988 | United Kingdom | A61K 7/075 |
| WO91/15186 | 1/1991 | WIPO . | |
| WO91/15187 | 3/1991 | WIPO . | |
| WO91/15185 | 6/1991 | WIPO . | |
| WO92/21319 | 3/1992 | WIPO . | |
| WO92/16187 | 5/1992 | WIPO . | |

*Primary Examiner*—Salle M. Gardner
*Attorney, Agent, or Firm*—Richard J. Ancel

[57] ABSTRACT

Hair rinse compositions, in emulsion or dispersion form, which condition the hair and facilitates setting thereof, includes a hair conditioning and emulsifying cationic compound, a water insoluble acrylic or acrylate polymer and a solvent which is a stabilizing and compatibilizing proportion of the composition comprising a higher aliphatic alcohol and/or alcohol ethoxylate, in an aqueous medium. The cationic compound is a quarternary ammonium salt preferably a higher alkyl trimethyl ammonium chloride and the polymer is preferably an acrylamide acrylate copolymer. Preferably solvents in the compositions are $C_{9-20}$ aliphatic alcohols and/or $C_{9-20}$ alcohol ethoxylates having less than 2 ethoxy groups per mole.

The preferred emulsion, which is normally of the oil-in-water type, preferably includes propylene glycol and a nonionic surfactant, and the aqueous medium is preferably water, or is essentially water. The invention also includes processes for making and using the invented hair rinse compositions.

3 Claims, No Drawings

CONDITIONING RINSE COMPOSITIONS WHICH FACILITATES SETTING OF HAIR

SPECIFICATION

This is a divisional of application Ser. No. 08/268,993 filed Jun. 30, 1994 which is a continuation of Ser. No. 08/049,194 filed Apr. 19, 1993, abandoned, which is a continuation-in-part of Ser. No. 07/822,377 filed Jan. 17, 1992, abandoned, which is a continuation-in-part of Ser. No. 07/768,144 filed Sep. 30, 1991, abandoned.

FIELD OF THE INVENTION

This invention relates to hair rinse compositions, which, in addition to conditioning the hair to which it has been applied and from which it has been rinsed, improves its body and settability. Thus, in a single application of the invented hair rinse one can obtain hair treatment benefits that formerly required a first application of a Conditioning rinse, followed by rinsing and then by spraying on the hair of a hair spray or emulsion or application to the hair of a setting liquid, gel or mousse.

BACKGROUND ART

Prior to the present invention it had often been found that utilization of a conditioning rinse, while it made the treated hair easier to comb, decreased objectionable "flyaway" and softened it to the touch, did not sufficiently improve settability of the hair, so that use of a setting composition was necessitated. Therefore, subsequent to shampooing and conditioning and rinsing it has been customary to apply a setting composition to the conditioned hair tresses or to the shaped hair, which is allowed to remain on the hair (not rinsed off). Such setting compositions facilitate setting of the hair by improving holding power of the hair shapes or curls, and giving it body (or stiffness), all of which help to retain it in set shape, after drying. Now such improved settability, together with conditioning, can be achieved by use of the invented rinse compositions, without the need for a separate application of a setting composition.

The discovery of the present conditioning rinses that improve settability of hair was surprising because two of the materials employed, quaternary ammonium salt and water insoluble acrylic (or acrylate) polymer, normally being oppositely charged, would be expected to react detrimentally. Applicants have discovered that in the presence of solvents comprising higher aliphatic alcohols and/or alcohol ethoxylates having on average less than 2 ethoxy groups per mole, an aqueous oil-in-water emulsion (or dispersion) can be made of the quaternary ammonium salt (quat) and the polymer, and that the quat and the polymer are substantive to the hair when applied to it in such emulsion (or dispersion) and remain on it even after rinsing, so that they can exert their conditioning and bodying actions on it. Hair treated with the invented composition combs easily and yet is of sufficient body or stiffness so that it is easily set, and remains in place afterward, obviating the need for application to the hair of a separate setting composition (which is not subjectable to rinsing). It is believed that the quat and the polymer form a complex which is adherent to the hair and imparts to it the properties of its components, the conditioning action of the quat and the bodying action of the polymer, but such theory has not yet been completely verified and it is not to be considered that applicants are bound by it. Additionally, a suitable surfactant, such as a nonionic surfactant (sometimes in mixture with an anionic surfactant) may serve as a wetting agent in the composition and improve the contacting of the hair by the composition, thereby improving conditioning and settability.

A search of the prior art has shown that quaternary ammonium compounds have been employed in hair conditioning compositions as hair conditioning agents. For example, U.S. Pat. No. 4,711,776 to Suzuki et al. describes certain quats in a hair rinse and U.S. Pat. No. 4,777,037 to Wagman et al. describes certain quats in a hair conditioning emulsion also containing silicones, higher fatty alcohol, surfactant and water. U.S. Pat. No. 4,997,641, issued to the present inventors, mentions conditioning shampoos containing quats, long chain alcohols, silicones and thickeners in shampoos based on certain anionic detergents. U.S. Pat. No. 4,196,190 to Gehman et al. relates to an acrylic polymer solution that can be employed for hair setting and U.S. Pat. No. 3,907,984 to Calvert et al. describes hair holding compositions that include acrylates, methacrylates, acrylamides and methacrylamides in water insoluble block copolymers, while U.S. Pat. No. 4,543,249 to Nelson describes a hair spray that contains methylmethacrylate/ methacrylic acid copolymers. In a BASF provisional technical information bulletin (Register 12), issued in 1989, Luviflex™VBM 35 is described as a PVP-acrylates copolymer which is useful in hair sprays, setting lotions and mousses as a film former, but it is said to be incompatible with cationic compounds. U.S. Pat. No. 5,019,377 to Torgerson describes hair styling compositions including neutralized polymer components of acrylic acid and methacrylic acid and their salts, but these neutralized polymers are said to be incompatible with cationic materials. U.S. Pat. No. 4,741,855 describes a conditioning shampoo that may contain a nonionic surfactant, a water insoluble silicone, a quaternary ammonium chloride, ethylene glycol and water.

From the prior art mentioned it is seen that various quaternary ammonium salts, nonionic wetting agents, acrylic and acrylate polymers, and long chain alcohols have been employed in hair treating compositions, including rinses and shampoos, for conditioning or bodying the hair, however none of these references teach the combination of a quaternary ammonium salt hair conditioning agent, acrylic or acrylate polymer and long chain alcohol in an aqueous hair rinse that conditions hair and improves its body to facilitate setting thereof. This invention is directed to the provision of such hair rinse compositions that comprise quaternary ammonium salts, acrylic or acrylate polymers and solvents comprising long chain alcohols and/or alcohol ethoxylates. It would be appreciated that advantage over known conditioning rinse compositions would be obtained by providing such hair rinse compositions which improve both the hair's body and settability.

In addition, the prior art does not show that the solvent component comprising higher alcohols and/or alcohol ethoxylates play an important role in making the quat compatible with the polymer and at the same time improves both the conditioning and bodying effects of the active components. This is important because the solvent, in addition to helping to stabilize the rinse emulsion, also helps to control the sorption by and/or deposition on the hair of the quat and the polymer (or the complex, which it might help to form), leading to a desired balance of conditioning and bodying effects. Without the particular solvents present in the described rinses conditioning and bodying effects have been found to be diminished or in some cases such effects are unbalanced, with bodying (settability) being adversely affected. The solvent itself acts as a conditioning agent but in the present compositions also performs a valuable function in compatibilizing the quat and polymer so that they form an emulsion (which term is intended to include dispersions, too), with the polymer thereof being of the right water insolubility to best hold to the hair.

Accordingly, it is a broad object of the invention to provide hair rinse compositions which in addition to conditioning the hair to which it has been applied and from which it has been rinsed, improves its body and settability.

A more specific object of the invention is to provide hair rinse compositions in oil-in-water emulsion or dispersion form comprising a hair conditioning and emulsifying proportion of a cationic hair conditioning agent, a hair setting proportion of a water insoluble hair setting acrylic or acrylate polymer and a solvent which is a stabilizing and compatibilizing proportion of the composition comprising a higher aliphatic alcohol and/or alcohol ethoxylates, in an aqueous medium.

Another object of the invention is to provide hair rinse compositions which improve settability and conditioning in a single application.

Another object of the invention is to provide a process for manufacture of the hair rinse compositions in the form of oil-in-water emulsions.

A further specific object of the invention is to provide a simplified process for simultaneously conditioning hair and making it more readily settable.

DISCLOSURE OF THE INVENTION

In the present invention, these purpose, as well as others which will be apparent, are achieved generally by providing hair rinse compositions which in addition to conditioning hair improves its body and settability. The hair rinse compositions, in oil-in-water emulsion or dispersion form, comprise a hair conditioning and emulsifying proportion of a cationic hair conditioning agent, a hair setting proportion of a water insoluble hair setting acrylic or acrylate polymer, and a solvent which is a stabilizing and compatibilizing proportion of the compositions comprising a higher aliphatic alcohol and/or alcohol ethoxylates, in an aqueous medium.

The primary components of the invented rinses are a cationic hair conditioning agent, an acrylic or acrylate polymer and a solvent comprising a higher aliphatic alcohol and/or alcohol ethoxylates. The cationic hair conditioning agent is preferably a quaternary ammonium salt and possesses hair conditioning and emulsifying and/or dispersing effects. The quaternary ammonium salts (quats) that are preferably utilized are alkyl compounds, with at least one higher alkyl and at least one lower alkyl on the quaternary nitrogen. Some examples of preferred quats are cetyl (or hexadecyl) trimethyl ammonium chloride, tallowyl trimethyl ammonium chloride, hydrogenated tallowyl trimethyl ammonium chloride, lauryl (or dodecyl) ammonium chloride, stearyl (or octadecyl) trimethyl ammonium chloride, and corresponding bromides, when acceptable. Other cationic compounds, such as corresponding amine hydrochlorides, may also be used in the invention compositions.

The polymer component of the invented rinse compositions are normally water insoluble acrylic or acrylate polymers. The presence of the quat is instrumental in helping to regulate polymer or complex solubility, and tends to insolubilize the polymeric material. Among the various types of acrylic or acrylate polymers that may be employed in accordance with the present invention are polyacrylates, polymethacrylates, corresponding acrylic and methacrylic polymers, acrylic/methacrylic copolymers, octylacrylamide/ acrylate copolymers, and vinylpyrrolidone/acrylate or PVP acrylate copolymers, such as vinylpyrrolidone/t-butyl acrylate copolymers, which are only representative of this class of polymers.

The acrylic polymers may also be partially neutralized to regulate the extent of water insolubility (or solubility) thereof, which can affect the stability of the emulsion rinse and the substantivity to the hair of the quat and polymer (or quat/polymer complex), as well as the nature of any complex formed with the quat (and the solvent).

The solvents employed in the invention are nonaqueous $C_{9-20}$ aliphatic alcohols and/or $C_{9-20}$ alcohol ethoxylates. The presence of the solvent helps to solubilize the polymer in the rinse compositions and also serves to stabilize the emulsion or dispersion made. The alcohols are preferably alkanols and more preferably linear fatty alcohols. The alcohol ethoxylates have on average less than 2 ethoxy groups per mole.

Preferred alcohol solvents are $C_{9-14}$ alcohols, more preferably dodecyl alcohol, such as lauryl alcohol, and tetradecanol, but other alcohols are also employable. Preferred alcohol ethoxylates are $C_{10-20}$ alcohol ethoxylates and more preferably $C_{14-20}$ alcohol ethoxylates. Solvent mixtures comprising both alcohols and alcohol ethoxylates are also used in the invention. Preferred mixtures are comprised of $C_{10-20}$ alcohols and $C_{14-20}$ $C_{10-20}$ alcohol ethoxylates, and more preferably $C_{14-20}$ alcohols and alcohol ethoxylates, in the ratio of 2:1 to 1:3. A preferred solvent mixture comprises tetradecanol and tetradeceth-1, which has an average degree of ethoxylation of one, in the ratio of 2:1.

The $C_{14-20}$ alcohols and/or $C_{14-20}$ alcohol ethoxylates have boiling points greater than 280° C., preferably between 280° and 380° C. and have solubilities in water at 25° C. less than 0.1% and preferably less than 0.01%. The $C_{9-13}$ alcohols have boiling points in the range of 200°–300° C., preferably less than 280° C. and have solubilities in water at 25° C. less than 0.1% and preferably, less than 0.01%.

Effectiveness of the invented rinses are enhanced by the presence of nonionic surfactants, anionic surfactants and propylene glycol. Various adjuvants including perfumes, dyes, brighteners, anti-dandruff agents, bactericides, fungicides, ultraviolet light absorbers, silicone agents and thickeners may also be included in the invented compositions.

The proportions of the various components of the invention rinses are 0.5 to 5% of the cationic component, preferably 1 to 4%; 0.5 to 6% of the acrylic or acrylate polymer, preferably 1 to 4%; and 1.5 to 10%, preferably 3 to 8% of the solvent component. The water content of the hair compositions are usually at least 80%, preferably from 80 to 97.5%. Ordinary adjuvants which may be present in the invention rinses replace part of the water content. The surface active wetting agents and propylene glycol, which are optional additional components of the compositions, if present are in the range of 0.1 to 0.75% and 1 to 5%, respectively.

Surprisingly, the invented rinse compositions, even after rinsing of the hair with water after application of the composition to the hair, deposit on the hair enough of the quaternary ammonium salt to condition the hair (facilitating combing thereof) and deposit enough of the copolymer to give the hair body and facilitate setting thereof in a desired hairstyle. Such desirable results are surprising because usually conditioning agents cause a diminution in settability and bodying agents diminish conditioning. The present invention is a noteworthy advance in the hair treating art because it permits one-step conditioning and settability, improves (bodying) rinse application and obviates any separate application of a spray, mousse or other setting composition to the hair after a rinse treatment to improve hair conditioning, the components of which setting compositions (except those evaporated off) would otherwise remain on the hair.

Other objects, features and advantages of the present invention will be apparent when the detailed description of the preferred embodiments of the invention are considered.

DETAILED DESCRIPTION OF THE PREFERRED EMBODIMENTS

In accordance with the present invention a hair rinse composition in oil-in-water emulsion or dispersion form, which conditions the hair and facilitates setting thereof, comprises a hair conditioning and emulsifying proportion of a cationic compound preferably a quaternary ammonium salt (quat) hair conditioning agent, a hair setting proportion of a water insoluble hair setting acrylic or acrylate polymer, and a solvent which is a stabilizing and compatibilizing proportion of the compositions comprising a higher aliphatic alcohol and/or alcohol ethoxylates, in an aqueous medium. Also within the invention are processes for manufacturing and for using the invented compositions.

The primary components of the invented rinses are the quat, polymer and solvent, which will be described herein in that order. The quat may be any suitable quaternary ammonium salt, which possesses hair conditioning and emulsifying and/or dispersing effects. By hair conditioning is meant improving ease of wet and dry combing of the hair, especially wet combing, so that snarls are avoided or are comparatively easily untangled during combing of the hair, especially immediately after shampooing, and rinsing with an invented preparation. By emulsifying and/or dispersing is meant such action as makes the components of the rinse, especially the polymer, solvent and any other normally water insoluble components emulsifiable or dispersible so that they remain suspended in the aqueous medium, without objectionable setting out or separation for considerable periods of time, e.g., 6 months or a year at room temperature, and the products described are considered to be stable.

The quaternary ammonium salts that are utilizable include those which have the desired hair conditioning properties and which also act as emulsifiers. Such emulsifying property is desirable, as in the preparations of the invented compositions in emulsion form, especially when the quantity of any other emulsifier present is inadequate for good emulsification. Other cationic compounds of similar properties may be substituted for the quats but usually the results will not be as satisfactory as when the described quats are employed. The quaternary ammonium salts that are preferably utilized are alkyl compounds, with at least one higher alkyl and at least one lower alkyl on the quaternary nitrogen. The salt-forming anion of the quat may be any such anion, including the various suitable halogens, sulfate and methosulfate, of which chloride is most preferred. A preferred quat is of the formula

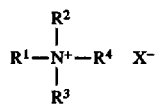  A)

wherein $R^1$ and $R^2$ are lower alkyl, of 1 to 4 carbon atoms, $R^3$ is either hydrogen or lower alkyl, $R^4$ is higher alkyl of 10 to 18 carbon atoms, and $X^-$ is a salt-forming anion.

Instead of employing such a mono-higher alkyl-containing quat one may use a mixture of it and a quat of the formula

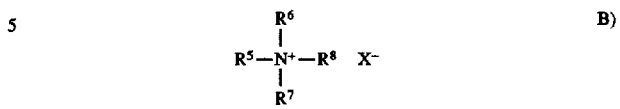 B)

wherein $R^5$ is hydrogen or lower alkyl, and $R^6$ is higher alkyl and $R^7$ and $R^8$ are both higher alkyls or one is higher alkyl and one is a lower alkyl, and $X^-$ is a salt-forming anion.

When mixtures of the quats of the given formula are present it will be preferred that the proportions thereof will be 1 to 9 parts of the A formula and 1 to 9 parts of the B formula, more preferably 5 to 9 parts of A and 1 to 5 parts of B. The preferred lower alkyl groups are methyl or ethyl groups, most preferably methyl, and the preferred higher alkyl groups are of 12 to 18 carbon atoms, more preferably lauryl, stearyl, cetyl, "tallowyl" and "hydrogenated tallowyl". Instead of alkyl substituents on the quaternary nitrogen other substituents may be employed, including lower alkoxy alkyls, poly-lower alkoxy alkyls, aryls, such as phenyl, and others that are known in the art.

The preferred anion of the quats is chlorine ion, although sometimes bromine ion may replace it, at least in part. Many such quats are mixtures and this specification and the claims should be interpreted to apply to such also, as well as to pure compounds, and similarly, descriptions herein of other components of the present compositions should be considered in the same manner.

Some examples of preferred quats are cetyl (or hexadecyl) trimethyl ammonium chloride, tallowyl trimethyl ammonium chloride, hydrogenated tallowyl trimethyl ammonium chloride, lauryl (or dodecyl) ammonium chloride, stearyl (or octadecyl) trimethyl ammonium chloride, and corresponding bromides, when acceptable. In some instances ethyl, n-propyl, isopropyl, n-butyl and sec-butyl may be substituted, preferably only in part, for some or all of the methyl groups of the preferred quats, and other higher alkyls may be similarly substituted for those disclosed herein. In making all such substitutions and in formulating the present rinses, in general, care should be exercised so that the particular quat/polymer combination and the proportion of quat:polymer are such as to make an emulsion or dispersion (which can also be in gel or other suitable physical form), which has the desired substantivity to the hair (and is of desired insolubility during rinsing), and possesses the desired balance of conditioning and bodying properties, so that after use of the rinse the hair is easily combed and yet is readily settable (and holds the set). For simplicity's sake reference herein will be to the preferred quats and to emulsions but it should be understood that other cationic compounds, such as corresponding amine hydrochlorides, may also be used, and dispersions are included within the term "emulsions", as employed herein.

The polymer component of the invented rinse compositions is one which may be characterized as a normally water insoluble acrylic or acrylate polymer. By normally water insoluble is meant that while it may be emulsifiable or dispersible it is insoluble in water alone. The solubility in water of the unneutralized polymer is desirably less than 0.1% and such solubilities may be diminished by the presence of quats. Such polymers have also been characterized as film-forming, which property is considered to be useful in helping treated hair develop more body and be more easily settable (and set retaining).

The acrylic polymers may be partially neutralized to regulate the extent of water insolubility (or solubility)

thereof, which can affect the stability of the emulsion rinse and the substantivity to the hair of the quat and polymer (or quat/polymer complex), as well as the nature of any complex formed with the quat (and the solvent).

By regulating the solubility of the polymer or the complex, which often can be done by partial neutralization thereof, one is able to produce a rinse which includes a polymer or complex which is insoluble enough in the rinsing operation to hold to the hair. Another advantage of partial neutralization of the polymer or complex is that it improves removal thereof on subsequent shampooing, preventing unwanted excessive build-up of deposited materials on the hair, which makes conditioning and bodying more controllable. The presence of the quat is also instrumental in helping to regulate polymer or complex solubility, and tends to insolubilize such polymeric material.

Among the various types of acrylic or acrylate polymers that may be employed in accordance with the present invention there may be specifically mentioned polyacrylates, polymethacrylates, corresponding acrylic and methacrylic polymers, acrylic/methacrylic copolymers, octylacrylamide/ acrylate copolymers, and vinylpyrrolidone/acrylate or PVP acrylate copolymers, such as vinylpyrrolidone/t-butyl acrylate copolymers, which are only representative of this class of polymers. Such polymers are available commercially or on an experimental basis under various trade names and from various manufacturers. For example, Versatyl®42, which is highly preferred copolymer component of the present compositions, is an octylacrylamide/acrylates copolymer, and is available from National Starch Corp., as are similar products under the trade identifications Dermacryl™-70 and National Starch™28-4979. Such octylacrylamide/acrylate copolymers may be made from octylacrylamide and one or more monomers of acrylic acid, methacrylic acid or simple esters thereof.

In addition other highly preferred copolymer components of the present compositions are a group comprising terpolymers of acrylic acid, ethyl acrylate and N-t-butyl acrylamide. Preferred copolymers of this group are Ultrahold®8 and Ultrahold®Strong manufactured by BASF A.G. Ultrahold®8 comprises 8% acrylic acid and is used as a film former and fixative in hair-care preparations. Ultrahold®Strong comprises 10% acrylic acid and provides a stronger hold than Ultrahold®8.

Also useful in the present compositions as polymer components thereof are Luviflex™VBM 35 and Luviflex™VBM 70, manufactured by BASF A.G., both of which are copolymers of vinylpyrrolidone, t-butyl acrylate and methacrylic acid, and Luviflex™VB (No. 23618/30/1), also made by BASF A.G., which is a copolymer of vinylpyrrolidone and t-butyl acrylate. Another copolymer of this general type is that sold under the name Amphomer® (octylacrylamide/acrylates/butylaminoethyl methacrylate polymer), which is made by National Starch. Co. Sometimes, to decrease polymer solubility in water, a carboxylic acid containing polymer, such as Amphomer®28-4910, which is sometimes considered to be of greater solubility than desired, can be reacted with a higher alkyl amine, such as Armeen®DM12D (N,N-dimethyl dodecyl amine), preferably during manufacture of the rinse composition. Such action improves the bodying effect of the resulting rinse on the hair.

The various acrylic or acrylate polymers or copolymers may be of a wide variety of molecular weights, which are considered to be within the range of 20,000 to 5,000,000, preferably 50,000 to 1,000,000, more preferably 80,000 to 400,000 and most preferably 100,000 to 200,000. However, instead of relying on the weights of the polymers it is preferred to describe the useful polymeric materials which are present in the invented compositions in a more functional manner, as those which will yield a conditioning and bodying rinse for the hair when in a rinse with quat and solvent. Of the described polymers the Versatyl®-42, Ultrahold®8 and Ultrahold®Strong are the best, on that basis, but by modifying proportions and the types of quats and solvents employed, and sometimes also by changing the wetting agent accordingly, good results are considered to be attainable with the other mentioned polymers and various other acrylic or acrylate polymers, too.

It may be noted that the polymers have been referred to as acrylic or acrylate polymers and such reference is deliberate because they may include free carboxylic acid groups or such groups may be neutralized, as described above. Also, such carboxylic groups may be esterified, as by lower alcohols, to form lower alcohol esters thereof. While polymers containing either free carboxylic acid moieties or neutralized acidic groups may be employed it has been found that often the best products, from the viewpoint of possessing a good balance between effective conditioning and bodying properties, are those which are partially neutralized.

In compositions containing solvents comprising $C_{9-20}$ alcohols and/or $C_{9-20}$ alcohol ethoxylates such neutralization is normally to the extent of 5 to 100%. Where the solvent is a $C_{13-20}$ alcohol and/or $C_{13-20}$ alcohol ethoxylate having less than 2 ethoxy groups per mole, such partial neutralization is preferably 5 to 50% and more preferably 5 to 15%. In compositions containing solvents comprising $C_{9-20}$ alcohols such partial neutralization is normally to the extent of 30 to 90%, preferably 40 to 75%, more preferably 40 to 65%, and for the preferred octylacrylamide/acrylate copolymer, about 48% and for the preferred terpolymers of acrylic acid, ethyl acrylate and N-t-butyl acrylamide 40 to 65%.

By partial neutralization is meant that the acid number or acidity of the polymer is reduced by a percentage in the range of or like those given above, e.g., from 1 to 5 milli-equivalents per gram to 0.6 to 3 me./g. Reduction of acidity of the polymer tends to make it less water insoluble but when esters of the acrylic or methacrylic acid are the monomers of the polymers and are completely neutralized it is possible to have a low acid number (including zero) and still have water insoluble polymers. In any case it is desirable to carefully match or balance the polymer type and solubility (or insolubility) with the quat and the solvent to make the best conditioning and bodying rinse.

The solvent helps to solubilize the polymer in the rinse composition and also serves to stabilize the emulsion or dispersion made and compatibilizes the quat and the polymer, which are of opposite charges (the quat being positively charged and the polymer being negatively charged, like human hair), thereby increasing both conditioning and bodying effects on the treated (and rinsed) hair.

The solvents employed in the invention are nonaqueous $C_{9-20}$ aliphatic alcohols and/or $C_{9-20}$ alcohol ethoxylates. The alcohols are preferably alkanols and more preferably linear fatty alcohols, but some branching of the alkanols may be permissible. The alcohol ethoxylates have on average less than 2 ethoxy groups per mole.

Preferred alcohol solvents are $C_{9-14}$ alcohols, more preferably dodecyl alcohol, such as lauryl alcohol, and tetradecanol, but other higher alcohols of 9 to 20 carbon atoms are also employable. Below 9 carbon atoms the alcohols are ineffective, and some are of unacceptable odor for a cosmetic product. Even the 9- and 10- carbon alcohols emit objectionable odors, as does the C-11 alcohol (but to a lesser extent), possibly because it contains some malodorous, $C_{10}$ compound.

Preferred alcohol ethoxylate solvents are $C_{10-20}$ alcohol ethoxylates and more preferably $C_{14-20}$ alcohol ethoxylates. Solvent mixtures comprising both alcohols and alcohol ethoxylates are also used in the invention compositions. Preferred mixtures are comprised of $C_{10-20}$ alcohols and $C_{10-20}$ alcohol ethoxylates, and more preferably $C_{14-20}$ alcohols and $C_{14-20}$ alcohol ethoxylates, in the ratio of 2:1 to 1:3. A preferred solvent mixture comprises tetradecanol and tetradeceth-1, which has an average degree of ethoxylation of one, in the ratio of 2:1.

All the solvents used in the compositions except C14-1EO (tetradeceth-1) are solids. The C14-1EO has a melting point between 20°–26° C. and is a mixture of solid and liquid phases. The solvent being in the solid phase makes the polymer less sticky on the hands and gives a better, less greasy feel to the hair.

The $C_{14-20}$ alcohols and/or $C_{14-20}$ alcohol ethoxylates have boiling points greater than 280° C., preferably between 280° and 380° C. and have solubilities in water at 25° C. less than 0.1% and preferably less than 0.01%. The $C_{9-13}$ alcohols have boiling points in the range of 200°–300° C., preferably less than 280° C. and have solubilities in water at 25° C. less than 0.1% and preferably less than 0.01%. The boiling point of $C_9$ (1-nonanol) is 213.5° C.; $C_{10}$ (1-decanol) is 229° C.; and $C_{11}$ (1-undecanol) is 243° C.

Preferred alcohols and alcohol ethoxylates used are from Vista Chemical Company, Austin, Texas. The tables below illustrate the % ethoxylation and % free alcohol of the alcohol ethoxylates and boiling points and solubility in water of some of the alcohols used as solvents in the compositions.

| ALFONIC ® ETHOXYLATE | % FREE AL- COHOL | % ETHOXYLATION | | | | | | | |
|---|---|---|---|---|---|---|---|---|---|
| | | 1 | 2 | 3 | 4 | 5 | 6 | 7 | 8 |
| 12-10 (12 1/2EO) | 68.4 | 19.9 | 9.2 | 1.2 | | | | | |
| 14-9 (14-1/2EO) | 71.0 | 17.6 | 7.0 | 2.1 | 1.0 | | | | |
| 16-8 (16-1/2EO) | 78.9 | 14.8 | 4.8 | 1.0 | | | | | |
| 18-7 (18-1/2EO) | 71.1 | 17.1 | 8.2 | 2.1 | | | | | |
| 12-19 (12-1EO) | 50.9 | 15.4 | 9.5 | 8.0 | 5.5 | 4.8 | 2.5 | 1.6 | 0.9 |
| 14-17 (14-1EO) | 49.3 | 16.4 | 10.6 | 7.7 | 5.2 | 4.3 | 2.5 | 1.7 | 1.0 |
| 16-15 (16-1EO) | 38.0 | 20.9 | 13.9 | 9.1 | 6.1 | 4.7 | 2.8 | 1.8 | 1.2 |
| 18-14 (18-1EO) | 33.0 | 25.4 | 15.3 | 9.6 | 6.0 | 3.7 | 2.4 | 1.6 | 1.0 |

The above ethoxylates begin to boil at the boiling points of the corresponding unethoxylated alcohols. After the free alcohols boil off, the boiling temperatures increase.

| ALFOL ® ALCOHOL | BOILING POINT °C. | SOLUBILITY IN WATER (g/ml) |
|---|---|---|
| 12 | 254–259 | 0.0016 |
| 14 | 298–301 | NIL |
| 16 | 330–332 | NIL |
| 18 | 350–354 | NIL |

The solvent appears to act like a cosolvent for the quat and polymer, stabilizing them and holding them both in suspension or emulsion form in the aqueous medium, but the solvent could also be a means for promoting formation of a complex of the quat and polymer, which complex is adherent to or sorbed by the hair and so is not completely rinsed off it with the rest of the rinse composition. Also the solvent could help the quat and polymer adhere to the hair, due to its film-forming action. Whatever the action of the solvent, it is an important component of the present rinses and increases their effectiveness markedly.

The water employed may be any clean water but deionized water is preferred. Normally it will be desirable for the water to be of a hardness less than 300 p.p.m., as $CaCO_3$, preferably less than 150 p.p.m. and more preferably less than 50 p.p.m. Usually the presence of any water soluble solvent material in the compositions will be avoided because such tend to diminish deposition to the quat and polymer (and solvent) on the hair, but a small proportion of lower alcohol solvent may sometimes be tolerated, e.g., up to 5%, when it is useful to dissolve a dye or when it is present in a component, as supplied, and is inconvenient or difficult to remove.

Although the four most important components of the present rinse compositions have been described, two other types of compounds are also helpful in increasing the effectiveness of the invented rinses. It has been found that a nonionic surfactant (which may be replaced or partially replaced by an anionic surfactant) which acts as a wetting agent, can also increase the hair conditioning effect of the present rinses without adversely affecting settability. It is surprising, even amazing, that such improved effects are obtainable with such a small proportion of surfactant in the invented rinses. Among the nonionic surfactants that are useful are various lower alkoxylated compounds, such as derivatives of ethylene oxide, sometimes with propylene oxide. Condensation products of ethylene oxide and higher fatty alcohols or of ethylene oxide and alkylphenols are useful wetting agents, and of these the higher fatty alcohol polyglycol ethers are preferred. The condensation products of higher alcohol and ethylene oxide will usually contain 3 to 10 ethoxy (or glycol) groups per mol, with the higher alcohol being of 8–14 carbon atoms. Preferably the alcohol will be of 9–11 carbon atoms and will be condensed with 6 or about 6 mols of ethylene oxide per mol (C 9-11 pareth-6).

In some instances it may be desirable to employ a mixture of nonionic and anionic surfactant wetting agents, in which case the proportions thereof will desirably be in the range of 1 to 10 parts of the nonionic surfactant to 3 to 1 part of the anionic surfactant, preferably about equal parts of each. While various anionic wetting agent surfactants may be used it is preferred to employ higher alcohol ethoxylate sulfates wherein the alcohol is of 12 to 18 carbon atoms, is condensed with 5 to 12 mols of ethylene oxide per mol, and the sulfate is a sodium salt. More preferably the anionic surfactant is a $C_{18}$ alcohol ethoxylate sulfate, sodium salt, wherein there are 8 mols or about 8 mols of ethylene oxide per mol of higher alcohol (sodium octadeceth-8 sulfate). In some instances the proportion of anionic wetting agent may be more than that of the nonionic wetting agent, when a mixture is present in the invented rinses, and sometimes the anionic surfactant may replace the nonionic one entirely. However, when such greater proportions of anionic surfactant are used it has been noted that the settability property of the preparation is diminished, which is usually undesirable.

Another component of the rinse which improves bodying of the hair and therefore is a desired part of the more effective formulas is propylene glycol. It is surprising that it has the described bodying effect in the present rinses because it is miscible with water, and because ethylene glycol and butylene glycol, homologues thereof, are ineffective.

Various adjuvants may be included in the invented compositions for particular purposes, such as perfumes, dyes, brighteners, anti-dandruff agents, bactericides, fungicides, ultraviolet light absorbers and thickeners, but care will be exercised when formulating such materials into the rinses that they do not interfere with the desired conditioning and bodying of the hair. Among such adjuvants may also be included silicone or silicone-like hair treating agents, such as trimethylsilylamodimethicone, cyclomethicone, dimethylsiloxane polymers and stearoxytrimethyl silane, which are available from Dow-Corning Corp. as or in products identified as Q2-7224, 344 (and 345) fluid, 200 fluid and Q5-0158 wax, respectively, which can serve to improve conditioning without seriously adversely affecting bodying when proportions in the range of 0.1 to 1% are employed in applicants' rinses. When such materials are used care will be exercised to make sure that the amount thereof employed does not seriously adversely affect bodying ability of the rinse.

While it is considered that the invention is broad enough to require only functional limitations, especially with respect to the proportions of the quat, polymer and solvent that result in a rinse which satisfactorily and surprisingly conditions the hair and gives it body so that it is more readily settable and holds the set given, normally the various components of these rinses will be in certain preferred ranges of proportions. Thus, for the quat, the invented compositions will normally contain 0.5 to 5% thereof, preferably 1 to 4%, more preferably 1 to 3%, and most preferably 2 or about 2%. Such proportions, in conjunction with the desired proportions of polymer and solvent, result in best balancing of conditioning and setting actions being obtainable from the invented rinses. The content of acrylic or acrylate polymer in the present rinses will usually be in the range of 0.5 to 6%, preferably being in the range of 1 to 4%, more preferably 1 to 2%, and most preferably 1.5% or about 1.5%. The solvent content is normally in the range of 1.5 to 10%, preferably in the range of 3 to 8%, more preferably 5 to 7% and most preferably is 6% or about 6%.

In the preferred compositions containing the mentioned three important components and waters, which compositions may also contain propylene glycol and wetting agent(s), it is often most preferred to employ a mixture of about equal parts of lauryl trimethylammonium chloride and cetyl trimethylammonium chloride as the quat, with an acrylamide acrylate copolymer, most preferably either an octylacrylamide/acrylate copolymer, such as Versatyl®42, or a terpolymer of acrylic acid, ethyl acrylate and N-t-butyl acrylamide such as Ultrahold®8 or Ultrahold®Strong, as the polymer, and $C_{10-14}$ alcohol, most preferably dodecyl (or lauryl) alcohol or tetradecanol, as the higher alcohol and/or a $C_{10-20}$ alcohol ethoxylate, preferably tetradeceth-1, with an average- degree of ethoxylation of one. The aqueous medium in which the quat, polymer and solvent are present in the invented rinses is mostly water and on a composition basis the water content is usually at least 80%. Ranges of water contents, from less preferred to more preferred ranges, are 80 to 97.5%, 80 to 95% and 80 to 89.5%, with 87.8% or 89% or about such percentages being most preferred (not including any allowances for any ordinary adjuvants that may also be present, which will replace part of the water content.

Two optional but very useful additional components, which are not considered to be ordinary adjuvants, are surface active wetting agent(s) and propylene glycol. The surfactant content is usually in the range of 0.1 to 0.5%, preferably 0.1 to 0.3% and most preferably is 0.2 or about 0.2%. When the surfactant includes anionic surfactant, as well as nonionic surfactant, the ratio of one to the other will preferably be in the range of 1:4 to 4:1, more preferably 1:2 to 2:1 and most preferably will be 1:1 or about 1:1. The propylene glycol content will usually be in the range of 1 to 5%, preferably 2 to 4%, more preferably 2 to 3% and most preferably 2.5% or about 2.5%. Any adjuvants present, including any small proportion of solvent, e.g., ethanol, will normally be limited to no more than 5 or 10% of the rinse and preferably will be in the range of 0.1 to 3% thereof. When only perfume is present as such an adjuvant the proportion thereof will usually be no more than 1% and often will be in the range of 0.1 to 0.75%.

The rinse compositions may be made by a comparatively simple procedure, which yields stable products which are attractively opaque in appearance and are effective conditioning and bodying agents. In such a procedure an oil-in-water emulsion is made by making separate water and oil phase mixtures of the rinse components, with the water and a proportion of quat (such as about a half) in the water phase mix and with the polymer, solvent and the rest of the quat in the oil phase mix. When, as is most desirable, surfactant(s) and propylene glycol are also present, the surfactant(s) will be in the water phase mix and the propylene glycol will be in the oil phase mix. Both mixes are then heated separately to a temperature in the range of 75° to 90° C., preferably 80° to 85° C., and the oil phase mix is added slowly to the water phase mix, with stirring, which causes formation of the desired stable opaque oil-in-water emulsion, which is then cooled to room temperature (usually in the range of 20° to 30° C.). During cooling or afterward a solution of alkali, which may be sodium or potassium hydroxide or other alkaline material, may be added to the emulsion (or dispersion, which may be a more proper term because part of the "liquid phase" can be solid polymer) in relatively small proportion to partially neutralize the polymer. Alternatively, the polymer could be partially neutralized before commencement of the formulation.

After cooling, any perfume and other adjuvants which are unstable or undesirably reactive and higher temperatures may be added. If other adjuvants are to be present they may be added to the appropriate hydrophilic or lipophilic mixes before heating if they are heat stable and do not interfere with the formation of the emulsion; otherwise, they will be added after making of the emulsion has been effected. The rinse composition resulting is of a viscosity in the range of 500 to 10,000 centipoises, preferably 1,000 to 5,000 centipoises, more preferably 2,000 to 3,500 cp., is of attractive opaque and "glossy" appearance, is of a pH in the range of 3-7, preferably 3.5 to 6, and is an effective conditioning and bodying rinse for human hair, as has been established in actual use and by laboratory tests and evaluations.

Although it is highly preferred to make oil-in-water emulsion rinses by the procedure described above, it is also possible to make a water-in-oil emulsion and "invert" it to oil-in-water form. This can be accomplished, using the appropriate polymer, quat and solvent, for example, by mixing 0.2 part of oleth-2 wetting agent with 3.55 parts of water and heating to 85 ° C., dissolving the polymer in the solvent by adding 1.5 parts of either octylacrylamide/acrylate copolymer or a terpolymer of acrylic acid, ethyl acrylate and N-t-butyl acrylamide to 6 parts of solvent and heating to 82° C., then adding 2.5 parts of propylene glycol, 1 part of laurtrimonium chloride and 0.25 part of tricetylmonium chloride to the oil phase and heating again to 82 ° C. The water phase is then added to the oil phase while stirring, thus forming a water-in-oil emulsion, which is inverted to an oil-in-water emulsion by adding it to 85 parts of water, also at 82° C., with stirring. The resulting oil-inwater emulsion is cooled to 25° C. and is ready for use as a stable conditioning and bodying hair rinse.

In use, the rinse is applied to the hair on the head after normal shampooing and rinsing. The amount applied will normally be from 1 to 50 milliliters, preferably 1 to 30 ml., depending on hair to be conditioned, and the rinse will be allowed to be in contact with the hair for ½ to 5 minutes, preferably ½ to 3 minutes and more preferably for 1 minute or about 1 minute. It is a feature of this invention that the contact time with the hair need not be lengthy (which increases consumer acceptance of the product) and, in fact, it is possible to obtain good effects from the rinse by removing it by rinsing immediately after completion of application of it to the hair to be treated. The rinse water employed is desirably of a temperature in the range of 25° to 50° C., preferably 30° to 45° C., e.g. 49° C. The result of the application and rinsing off of the applied rinse by the procedure described herein is that the treated hair is satisfactorily conditioned and combs easily, while at the same time it is of improved body, stiffer in feel, more readily settable and capable of holding a set better, compared to similar rinses that do not contain applicants' quat, polymer and solvent. Such advantages are obtained by use of this novel and unobvious product in a one-step rinse application, without any requirement for rinse conditioning of the hair with subsequent application of a bodying agent.

The following examples illustrate various aspects of the invention but are not to be interpreted as limiting it. Unless otherwise indicated all parts are by weight and all temperatures are in °C.

EXAMPLE 1

| Component | Percent (by weight) |
| --- | --- |
| * C9–11 Pareth-6 | 0.2 |
| ** Cetrimonium chloride | 1.0 |
| Deionized water | 87.8 |
| Lauryl alcohol | 6.0 |
| + Octylacrylamide/acrylates copolymer | 1.5 |
| Propylene glycol | 2.5 |
| ++ Laurtrimonium chloride | 1.0 |
| | 100.0 |

* Ethoxylated $C_{9-11}$ alcohol af 6 mols of ethylene oxide per mol
** Cetyl trimethylammonium chloride
+ Versatyl ®42 (National Starch Corp., M.W. in range of 150,000 to 200,000)
++ Lauryl trimethylammonium chloride The first three components of the above formula are mixed together and heated to 82° C. The solvent (lauryl alcohol) and polymer are separately heated to 82° C., at which temperature the polymer is in the liquid state. The remaining components are then added to the polymer solution and heating continued to 82° C. The second mixture is then mixed with the first, so as to form the desired emulsion or dispersion, which is then cooled to room temperature, about 25° C. During the cooling aqueous potassium hydroxide (KOH) solution is added to partially neutralize the carboxylic acid groups of the polymer, to the extent of 48% neutralization thereof. After cooling to room temperature the rinse resulting is of a pH of about 6 and its viscosity is about 3,500 centipoises, as measured by a Brookfield viscometer, Model RVTD, using a No. 3 spindle rotating at 20 r.p.m.

The rinse preparation resulting is an attractive opaque "shiny" or "glistening" liquid which is pourable from a comparatively narrow-necked container. When perfumed with conventional perfumes that are employed for such products it is clean smelling and fragrant, and it transmits that fragrance to the hair treated with it. When it is tested for conditioning action and for setting action by a panel of scientist/evaluators experienced in evaluating such products it is found to make the hair rinsed with it easy to comb and desirably settable, receiving averaged ratings of 3.5 for both characteristics, on scales that run from 1 to 5, with hard combing being 1, very easy combing being 5, not stiff (not settable) being 1 and very readily settable being 5. In these tests the tresses of human hair, which weigh 3.5 grams each, were shampooed, rinsed with water, treated with two ml. of the described rinse for one minute, rinsed with warm water (about 30° C.) and dried. The tresses were then examined by the trained evaluators and were tested by them for combability and stiffness (considered to be a test of settability because stiffer hair takes a set better). The evaluations were averaged and rounded off to the nearest half unit. In actual use of the described composition, testing it on hair on the head during showering, shampooing and setting, similar good results are obtainable. In actual uses of the rinses each rinse composition is allowed to be in contact with the hair for one minute and is rinsed off with water that is tepid, at a temperature in the range of 30° to 45° C., but good effects are obtained with even lower contact times, too.

When the formula is remanufactured and reevaluated the laboratory results and actual use results are about the same, with the conditioning being even better, indicating that an average value of about 4 for conditioning (ease of combing) might be more appropriate. When the nonionic wetting agent is replaced by sodium octadeth-8 sulfate there are slight changes in the testing results, with conditioning being increased and settability being decreased. Use of equal parts (0.1% each) of the anionic and nonionic surfactants results in lower ratings than the uses of nonionic surfactants alone, which (nonionic surfactant alone) is preferred.

In a variation on the principal formula given in this example the copolymer is completely neutralized with KOH, instead of being partially neutralized. Conditioning and settability ratings resulting are 3.0 and 2.5, respectively.

When the principal formula is changed by replacing the C9-11 pareth-6 with sodium deceth-3 sulfate and not neutralizing the copolymer a combing rating of 2.0 and a stiffness rating of 3.5 are obtained, which become 2.5 and 3.0, respectively, when the copolymer is neutralized to the extent of 48%, which also indicates that neutralization diminishes settability (and improves conditioning).

EXAMPLE 2

| Component | Percent (by weight) |
| --- | --- |
| * C9–11 Pareth-6 | 0.2 |
| *** Tallow trimonium chloride | 1.0 |
| Deionized water | 87.8 |
| Lauryl alcohol | 6.0 |
| + Octylacrylamide/acrylates copolymer | 1.5 |
| Propylene glycol | 2.5 |
| ++ Laurtrimonium chloride | 1.0 |
| | 100.0 |

* Ethoxylated $C_{9-11}$ alcohol of 6 mols of ethylene oxide per mol
*** Tallowalkyl trimethylammonium chloride
+ Versatyl ®42 (National Starch Corp., M.W. in range of 150,000 to 200,000)
++ Lauryl trimethylammonium chloride The rinse composition of this example is made in the same manner as described in EXAMPLE 1 and is tested for conditioning and settability in the same way, too. By the laboratory test it is awarded ratings of 4.0 and 4.5 for conditioning and settability, respectively, indicating that it is an excellent rinse for applicants' purposes. Similar results are obtainable when the tallow trimonium chloride is replaced by cetrimonium chloride. Such experimental results are confirmed by actual testing on human hair on the head, when the amount of rinse composition applied to the hair is about ½ ounce (about 14 grams) and it is rinsed off with tepid water after about a minute's contact with the hair.

EXAMPLE 3

| Component | Percent (by weight) |
|---|---|
| **** Oleth-2 | 0.2 |
| ** Cetrimoniumn chloride | 0.1 |
| Deionized water | 87.8 |
| Lauryl alcohol | 6.0 |
| + Octylacrylamide/acrylates copolymer | 1.5 |
| Propylene glycol | 2.5 |
| ++ Laurtrimonium chloride | 1.0 |
| | 100.0 |

**** Diethoxylated oleyl alcohol
** Cetyl trimethylammonium chloride
+ Versatyl ®42 (National Starch Corp., M.W. in range of 150,000 to 200,000)
++ Lauryl trimethylammonium chloride The rinse composition of this example is made and tested in the same manner as described for the compositions of EXAMPLES 1 and 2 and is rated at 3.0 for conditioning and 3.5 for stiffness (or settability). The formula is the same as that of EXAMPLE 1 except for the replacement of the C9-11 Pareth-6 nonionic wetting agent with Oleth-2, which apparently indicates that the more ethoxylated lower (relatively) alcohol promotes conditioning more than does the less ethoxylated higher alcohol in such compositions.

When this formula is changed by replacing 7.5 parts of water with 3 parts of lauryl alcohol and 4.5 parts of copolymer ratings of 3.0 and 3.0 are obtained, showing that increasing such proportions of the higher alcohol and hair stiffening copolymer do not improve conditioning and settability. When the given principal formula of this example is changed by eliminating the Oleth-2 from the formulation (replacing it with water) ratings of 3.0 and 3.0 are obtained, indicating that settability has been determined. Removal of the cetrimonium chloride from the formula and replacement of it with 0.05 part of Dow-Corning Q2-7224 conditioning agent (35% nonionic emulsion of an amine-functional silicone polymer) and 0.95% of water, with the Q2-7224 being added in the "oil phase", results in ratings of 4.0 and 2.5, respectively, showing that this silicone hair conditioning agent increases conditioning when it replaces quat conditioner but also that it reduces stiffness (or settability).

EXAMPLE 4

| Component | Percent (by weight) |
|---|---|
| **** Oleth-2 | 0.2 |
| ** Cetrimonium chloride | 1.0 |
| Deionized water | 87.8 |
| Lauryl alcohol | 6.0 |
| +++ Octylacrylamide/acrylates/ butylaminoethyl methacrylate polymer | 1.5 |
| Propylene Glycol | 2.5 |
| ++ Laurtrimonium chloride | 1.0 |
| | 100.0 |

**** Diethoxylated oleyl alcohol
** Cetyl trimethylammonium chloride
+++ Amphomer ®(National Starch Corp., M.W. in range of 100,00 to 150,000)
++ Lauryl trimethylammonium chloride The rinse composition of this example is made by the same procedure previously described in EXAMPLES 1–3 except that it is neutralized to 50% of the polymer capacity, after which it is tested by the same tests for conditioning and setting properties on human hair. It is found that the ratings are 4.0 and 3.0, respectively (conditioning and settability), indicating that the rinse composition is useful as a one-step preparation for conditioning and bodying the hair.

EXAMPLE 5

| Component | Percent (by weight) |
|---|---|
| **** Oleth-2 | 0.2 |
| Deionized water | 88.5 |
| Lauryl alcohol | 6.0 |
| ++++ Copolymer of vinylpyrrolidone and t-butyl acrylate | 2.0 |
| Propylene glycol | 2.5 |
| ++ Laurtrimonium chloride | 1.0 |
| ° Stearoxytrimethylsilane (and stearyl alcohol) | 0.25 |
| | 100.00 |

**** Diethoxylated oleyl alcohol
++++ Luviflex ™VB (No. 23618/30/1, manufactured by BASF A.G.)
++ Lauryl trimethylammonium chloride
° Dow-Corning ®Q5-0158A wax The above formula is of a product that is made and tested by the procedures described in the previous examples, and the test results are 4.0 and 3.5 for conditioning and stiffness, respectively.

EXAMPLE 6

| Component | Percent (by weight) |
|---|---|
| **** Oleth-2 | 0.2 |
| Deionized water | 86.8 |
| Lauryl alcohol | 6.0 |
| + Octylacrylamide/acrylates copolymer | 1.5 |
| Propylene glycol | 2.5 |
| ++ Laurtrimonium chloride | 1.0 |
| °° Trimethylsilylamodimethicone (35% emulsion,which includes Octoxynol-40, Isolaureth-6 and propylene glycol) | 1.0 |
| °°° Distearyl dimonium chloride | 1.0 |
| | 100.0 |

**** Diethoxylated oleyl alcohol
+ Versatyl ® (National Starch Corp., M.W. in range of 150,000 to 200,000)
++ Lauryl trimethylammomium chloride
°° Dow-Corning ®Q2-7224 conditioning agent
°°° Distearyl dimethylammonium chloride The formula is made in the same manner as the previous working examples and is similarly tested, resulting in evaluations of 3.5 for both conditioning and stiffness. It is noted that in the formula a di-higher alkyl di-lower alkylammonium salt is present, together with a silicone conditioning agent, and the quat is omitted from the initial aqueous phase materials.

EXAMPLE 7

| Component | Percent (by weight) |
|---|---|
| * C9–11 Pareth-6 | 0.2 |
| ** Cetrimonium chloride | 1.0 |
| Deionized water | 87.8 |
| Lauryl alcohol | 6.0 |

17
-continued

| Component | Percent (by weight) |
|---|---|
| oooo Acrylamide/acrylate copolymer | 1.5 |
| Propylene glycol | 2.5 |
| ++ Laurtrimonium chloride | 1.0 |
| | 100.0 |

\* Ethoxylated $C_{9-11}$ alcohol of 6 mols of ethylene oxide per mol
\*\* Cetyl trimethylammonium chloride
oooo Ultrahold ®8 (BASF, A.G.)
++ Lauryl trimethylammonium chloride The rinse composition of this example is made in the same manner as the previous working examples, except that it is neutralized to 48% of the polymer capacity, after which it is tested by the same tests for conditioning and setting properties on human hair. It is found that the ratings are 4.0 and 3.5, for conditioning and stiffness, respectively.

EXAMPLE 8

| Component | Percent (by weight) |
|---|---|
| \* C9–11 Pareth-6 | 0.2 |
| \*\* Cetrimonium chloride | 1.0 |
| Deionized water | 87.8 |
| Lauryl alcohol | 6.0 |
| oooo Acrylamide/acrylate copolymer | 1.5 |
| Propylene glycol | 2.5 |
| ++ Laurtrimonium chloride | 1.0 |
| | 100.0 |

\* Ethoxylated $C_{9-11}$ alcohol of 6 mols of ethylene oxide per mol
\*\* Cetyl trimethylammonium chloride
oooo Ultrahold ®8 (BASF, A.G.)
++ Lauryl trimethylammonium chloride The rinse composition of this example is made in the same manner as the previous working examples, except that it is neutralized to 90% of the polymer capacity, after which it is tested by the same tests for conditioning and setting properties on human hair. It is found that the ratings are 4.0 and 2.5, for conditioning and stiffness, respectively.

EXAMPLE 9

| Component | Percent (by weight) |
|---|---|
| \* C9–11 Pareth-6 | 0.2 |
| Deionized water | 88.8 |
| Lauryl alcohol | 6.0 |
| oooo Acrylamide/acrylate copolymer | 1.5 |
| Propylene glycol | 2.5 |
| ++ Laurtrimonium chloride | 1.0 |
| | 100.0 |

\* Ethoxylated $C_{9-11}$ alcohol of 6 mols of ethylene oxide per mol
oooo Ultrahold ®8 (BASF, A.G.)
++ Lauryl trimethylammonium chloride The rinse composition of this example is made in the same manner as the previous working examples, except that it is neutralized to 48% of the polymer capacity, after which it is tested by the same tests for conditioning and setting properties on human hair. It is found that the ratings are 4.0 and 3.0, for conditioning and stiffness, respectively.

18
EXAMPLE 10

| Component | Percent (by weight) |
|---|---|
| \* C9–11 Pareth-6 | 0.2 |
| \*\* Cetrimonium chloride | 1.0 |
| Deionized water | 87.8 |
| ° 1-Tetradecanol | 4.0 |
| °° C-14 1EO (Tetradeceth-1) | 2.0 |
| + Octylacrylamide/acrylates copolymer | 1.5 |
| Propylene glycol | 2.5 |
| ++ Laurtrimonium chloride | 1.0 |
| | 100.0 |

\* Ethoxylated $C_{9-11}$ alcohol of 6 mols of ethylene oxide per mol
\*\* Cetyl trimethylammonium chloride
° Alfol ®14 alcohol (Vista Chemical Co.)
°° Alfonic 200 14–17 ethoxylate (Vista Chemical Co., ethoxylated tetradecanol (14), with an average degree of ethoxylation of one)
+ Versatyl ®42 (National Starch Corp., M.W. in range of 150,000 to 200,000)
++ Lauryl trimethylammonium chloride The solvent used is in this example is a mixture of a $C_{10-14}$ alkanol and $C_{10-14}$ alcohol ethoxylate, having one ethoxy group per mole, in the ratio of approximately 2:1.

The rinse composition of this example is made by the following phase inversion technique.

For the water phase, water is placed in a beaker with mixing and heating. During heating, the next components, the wetting agent and quat, are added one at a time while mixing until 82° C. is attained.

The other components are combined as a separate "oil" phase. This oil phase is begun by heating the solvent in a beaker while stirring. When the solvent temperature reaches 50° C. the polymer is added. The heating is continued until 82° C. is reached at which point the polymer is completely dispersed in the solvent. At this point the remaining ingredients of the oil phase are added and heating continued until 82° C. is reached once again.

While keeping the oil phase mixing and at 82° C., the water phase is slowly added to the oil phase such that substantial thickening occurs. As the water phase continues to be added, the emulsion then begins to thin. At this point the desired phase inversion has occurred. Once this has occurred, the emulsion can be added to the remaining amount of the water phase and mixed at 82° C. for five minutes after which the heat is removed.

During the cooling, at 32° C., aqueous potassium hydroxide is added to partially neutralize the carboxylic acid groups of the polymer to the desired neutralization thereof. In this example it is neutralized to 5% of the polymer capacity. The resulting rinse composition is of a pH of about 3.7 and its viscosity is about 2,000 cp.

The composition was tested by the same tests for conditioning and setting properties on human hair as in the previous examples. It is found that the ratings are 3.75 and 3.75, for conditioning and stiffness, respectively. Thus, the results using a mixture of alkanol and alkanol ethoxylates as the solvent provide the same desirable results as using the higher aliphatic alcohols illustrated in Examples 1 to 9.

EXAMPLE 11

| Component | Percent (by weight) |
|---|---|
| * C9–11 Pareth-6 | 0.2 |
| ** Cetrimonium chloride | 1.0 |
| Deionized water | 87.8 |
| ° 1-Tetradecanol | 4.0 |
| ∞ C-14 1EO (Tetradeceth-1) | 2.0 |
| + Octylacrylamide/acrylates copolymer | 1.5 |
| Propylene glycol | 2.5 |
| ++ Laurtrimonium chloride | 1.0 |
| | 100.0 |

* Ethoxylated $C_{9-11}$ alcohol of 6 mols of ethylene oxide per mol
** Cetyl trimethylammonium chloride
° Alfol ®14 alcohol (Vista Chemical Co.)
∞ Alfonic ®14–17 ethoxylate (Vista Chemical Co., ethoxylated tetradecanol (C14), with an average degree of ethoxylation of one)
+ Versatyl ®42 (National Starch Corp., M.W. in range of 150,000 to 200,000)
++ Lauryl trimethylammonium chloride The rinse composition of this example is made in a similar manner as the phase inversion technique in EXAMPLE 10, except that the polymer has not been neutralized. The solvent used is a mixture of a $C_{10-14}$ alkanol and $C_{10-14}$ alcohol ethoxylate, having one ethoxy group per mole, in the ratio of approximately 2:1. The composition was tested by the same tests for conditioning and setting properties on human hair as in the previous examples. The ratings for conditioning and stiffness are set forth in Table I.

EXAMPLE 12

| Component | Percent (by weight) |
|---|---|
| * C9–11 Pareth-6 | 0.2 |
| ** Cetrimonium chloride | 1.0 |
| Deionized water | 87.8 |
| ° 1-Tetradecanol | 4.0 |
| ∞ C-14 1EO (Tetradeceth-1) | 2.0 |
| + Octylacrylamide/acrylates copolymer | 1.5 |
| Propylene glycol | 2.5 |
| ++ Laurtrimonium chloride | 1.0 |
| | 100.0 |

* Ethoxylated $C_{9-11}$ alcohol of 6 mols of ethylene oxide per mol
** Cetyl trimethylammonium chloride
° Alfol ®14 alcohol (Vista Chemical Co.)
∞ Alfonic ®14–17 ethoxylate (Vista Chemical Co., ethoxylated tetradecanol (C14), with an average degree of ethoxylation of one)
+ Versatyl ®42 (National Starch Corp., M.W. in range of 150,000 to 200,000)
++ Lauryl trimethylammonium chloride The rinse composition of this example is made in a similar manner as the phase inversion technique in EXAMPLE 10, except that the it is neutralized to 10% of the polymer capacity. The solvent used is a mixture of a $C_{10-14}$ alkanol and $C_{10-14}$ alcohol ethoxylate, having one ethoxy group per mole, in the ratio of approximately 2:1. The resulting rinse composition is of a pH of about 4.0 and its viscosity is about 2,000 to 2,500 cp. The composition was tested by the same tests for conditioning and setting properties on human hair as in the previous examples. The ratings for conditioning and stiffness are set forth in Table I.

EXAMPLE 13

| Component | Percent (by weight) |
|---|---|
| * C9–11 Pareth-6 | 0.2 |
| ** Cetrimonium chloride | 1.0 |
| Deionized water | 87.8 |
| • 1-Tetradecanol | 4.0 |
| •• C-14 1EO (Tetradeceth-1) | 2.0 |
| + Octylacrylamide/acrylates copolymer | 1.5 |
| Propylene glycol | 2.5 |
| ++ Laurtrimonium chloride | 1.0 |
| | 100.0 |

* Ethoxylated $C_{9-11}$ alcohol of 6 mols of ethylene oxide per mol
** Cetyl trimethylammonium chloride
• Alfol ®14 alcohol (Vista Chemical Co.)
•• Alfonic ®14–17 ethoxylate (Vista Chemical Co., ethoxylated tetradecanol (C14), with an average degree of ethoxylation of one)
+ Versatyl ®42 (National Starch Corp., M.W. in range of 150,000 to 200,000)
++ Lauryl trimethylammonium chloride The rinse composition of this example is made in a similar manner as in EXAMPLE 1, except that the it is neutralized to 48% of the polymer capacity. The solvent used is a mixture of a $C_{10-14}$ alkanol and $C_{10-14}$ alcohol ethoxylate, having one ethoxy group per mole, in the ratio of approximately 2:1. The composition was tested by the same tests for conditioning and setting properties on human hair as in the previous examples. The ratings for conditioning and stiffness are set forth in Table I.

EXAMPLE 14

| Component | Percent (by weight) |
|---|---|
| * C9–11 Pareth-6 | 0.2 |
| ** Cetrimonium chloride | 1.0 |
| ▲ Protachem GMS 165 | 1.0 |
| Deionized water | 87.8 |
| • 1-Tetradecanol | 4.0 |
| •• C-14 1EO (Tetradeceth-1) | 2.0 |
| + Octylacrylamide/acrylates copolymer | 1.5 |
| Propylene glycol | 2.5 |
| | 100.0 |

* Ethoxylated $C_{9-11}$ alcohol of 6 mols of ethylene oxide per mol
** Cetyl trimethylammonium chloride
▲ Protachem GMS 165 (Protameen Chemicals, Inc., glycerol monostearate and polyoxyethylene stearate)
• Alfol ®14 alcohol (Vista Chemical Co.)
•• Alfonic ®14–17 ethoxylate (Vista Chemical Co., ethoxylated tetradecanol (C14), with an average degree of ethoxylation of one)
+ Versatyl ®42 (National Starch Corp., M.W. in range of 150,000 to 200,000)

The rinse composition of this example is made in a similar manner as in EXAMPLE 1, except that the it is neutralized to 48% of the polymer capacity. The solvent used is a mixture of a $C_{10-14}$ alkanol and $C_{10-14}$ alcohol ethoxylate, having one ethoxy group per mole, in the ratio of approximately 2:1. The presence of Protachem GMS 165 acts as an emulsifying and thickening agent of the composition increasing the viscosity to over 5,000 cp. The composition was tested by the same tests for conditioning and setting properties on human hair as in the previous examples. The ratings for conditioning and stiffness are set forth in Table I.

EXAMPLE 15

| Component | Percent (by weight) |
| --- | --- |
| * C9–11 Pareth-6 | 0.2 |
| ** Cetrimonium chloride | 1.0 |
| ▲ Protachem GMS 165 | 0.3 |
| Deionized water | 87.2 |
| • 1-Tetradecanol | 4.0 |
| •• C-14 1EO (Tetradeceth-1) | 2.0 |
| ▲▲ Acrylamide/acrylate copolymer | 1.5 |
| Propylene glycol | 2.5 |
| ++ Laurtrimonium chloride | 1.0 |
| ▲ Protachem GMS 165 | 0.3 |
| | 100.0 |

* Ethoxylated $C_{9-11}$ alcohol of 6 mols of ethylene oxide per mol
** Cetyl trimethylammonium chloride
▲ Protachem GMS 165 (Protameen Chemicals, Inc., glycerol monostearate and polyoxyethylene stearate)
• Alfol ®14 alcohol (Vista Chemical Co.)
•• Alfonic ®14-17 ethoxylate (Vista Chemical Co., ethoxylated tetradecanol (C14), with an average degree of ethoxylation of one)
▲▲ Ultrahold ®Strong (BASF, A.G., 10% carboxylic acid monomer)
++ Lauryl trimethylammonium chloride The rinse composition of this example is made in a similar manner as in EXAMPLE 1, except that the it is neutralized to 48% of the polymer capacity. The solvent used is a mixture of a $C_{10-14}$ alkanol and $C_{10-14}$ alcohol ethoxylate, having one ethoxy group per mole, in the ratio of approximately 2:1. The composition was tested by the same tests for conditioning and setting properties on human hair as in the previous examples. The ratings for conditioning and stiffness are set forth in Table I.

EXAMPLE 16

| Component | Percent (by weight) |
| --- | --- |
| * C9–11 Pareth-6 | 0.2 |
| ** Cetrimonium chloride | 1.0 |
| Deionized water | 87.8 |
| •• 1-Tridecanol | 3.0 |
| •••• C-16 1EO | 3.0 |
| + Octylacrylamide/acrylates copolymer | 1.5 |
| Propylene glycol | 2.5 |
| ++ Laurtrimonium chloride | 1.0 |
| | 100.0 |

* Ethoxylated $C_{9-11}$ alcohol of 6 mols of ethylene oxide per mol
** Cetyl trimethylammonium chloride
• Alfol ®13 alcohol (Vista Chemical Co.)
•••• Alfonic ®16-14 ethoxylate (Vista Chemical Co., ethoxylated hexadecanol (C16), with an average degree of ethoxylation of one)
+ Versatyl ®42 (National Starch Corp., M.W. in range of 150,000 to 200,000)
++ Lauryl trimethylammonium chloride The rinse composition of this example is made in a similar manner as in EXAMPLE 1, except that the it is neutralized to 48% of the poller capacity. The solvent used is a mixture of a $C_{10-14}$ alkanol and $C_{10-20}$ alcohol ethoxylate, having one ethoxy group per mole, in the ratio of approximately 1:1. The resulting rinse composition is of a pH of about 5.5 and its viscosity is about 3,500 cp. The composition was tested by the same tests for conditioning and setting properties on human hair as in the previous examples. The ratings for conditioning and stiffness are set forth in Table I.

EXAMPLE 17

| Component | Percent (by weight) |
| --- | --- |
| * C9–11 Pareth-6 | 0.2 |
| ** Cetrimonium chloride | 1.0 |
| Deionized water | 87.8 |
| ♦ C-18 ½EO | 6.0 |
| + Octylacrylamide/acrylates copolymer | 1.5 |
| Propylene glycol | 2.5 |
| ++ Laurtrimonium chloride | 1.0 |
| | 100.0 |

* Ethoxylated $C_{9-11}$ alcohol of 6 mols of ethylene oxide per mol
** Cetyl trimethylammonium chloride
♦ Alfonic ®18-7 ethoxylate (Vista Chemical Co., ethoxylated octadecanol (C18), with an average degree of ethoxylation of ½)
+ Versatyl ®42 (National Starch Corp., M.W. in range of 150,000 to 200,000)
++ Lauryl trimethylammonium chloride The rinse composition of this example is made in a similar manner as in EXAMPLE 1, except that the it is neutralized to 48% of the polymer capacity. The solvent used is a $C_{10-20}$ alcohol ethoxylate, having ½ ethoxy group per mole. The composition was tested by the same tests for conditioning and setting properties on human hair as in the previous examples. The ratings for conditioning and stiffness are set forth in Table I.

EXAMPLE 18

| Component | Percent (by weight) |
| --- | --- |
| * C9–11 Pareth-6 | 0.2 |
| ** Cetrimonium chloride | 1.0 |
| Deionized water | 87.8 |
| ♦♦ C-16 ½EO | 6.0 |
| + Octylacrylamide/acrylates copolymer | 1.5 |
| Propylene glycol | 2.5 |
| ++ Laurtrimonium chloride | 1.0 |
| | 100.0 |

* Ethoxylated $C_{9-11}$ alcohol of 6 mols of ethylene oxide per mol
** Cetyl trimethylammonium chloride
♦♦ Alfonic ®16-8 ethoxylate (Vista Chemical Co., ethoxylated hexadecanol (C16), with an average degree of ethoxylation of ½)
+ Versatyl ®42 (National Starch Corp., M.W. in range of 150,000 to 200,000)
++ Lauryl trimethylammonium chloride The rinse composition of this example is made in a similar manner as in EXAMPLE 1, except that the it is neutralized to 48% of the polymer capacity. The solvent used is a $C_{10-20}$ alcohol ethoxylate, having ½ ethoxy group per mole. The composition was tested by the same tests for conditioning and setting properties on human hair as in the previous examples. The ratings for conditioning and stiffness are set forth in Table I.

EXAMPLE 19

| Component | Percent (by weight) |
| --- | --- |
| * C9–11 Pareth-6 | 0.2 |
| ** Cetrimonium chloride | 1.0 |
| Deionized water | 87.8 |
| • 1-Tetradecanol | 3.0 |
| ♦♦♦ C-16 1EO | 3.0 |

-continued

| Component | Percent (by weight) |
|---|---|
| + Octylacrylamide/acrylates copolymer | 1.5 |
| Propylene glycol | 2.5 |
| ++ Laurtrimonium chloride | 1.0 |
| | 100.0 |

* Ethoxylated $C_{9-11}$ alcohol of 6 mols of ethylene oxide per mol
** Cetyl trimethylammonium chloride
• Alfol ®13 alcohol (Vista Chemical Co.)
♦♦♦ Alfonic ®16-14 ethoxylate (Vista Chemical Co., ethoxylated hexadecanol (C16), with an average degree of ethoxylation of one)
+ Versatyl ®42 (National Starch Corp., M.W. in range of 150,000 to 200,000)
++ Lauryl trimethylammonium chloride The rinse composition of this example is made in a similar manner as in EXAMPLE 1, except that the it is neutralized to 48% of the polymer capacity. The solvent used is a mixture of a $C_{10-14}$ alkanol and $C_{10-20}$ alcohol ethoxylate, having one ethoxy group per mole, in the ratio of approximately 1:1. The composition was tested by the same tests for conditioning and setting properties on human hair as in the previous examples. The ratings for conditioning and stiffness are set forth in Table I.

EXAMPLE 20

| Component | Percent (by weight) |
|---|---|
| * C9–11 Pareth-6 | 0.2 |
| ** Cetrimonium chloride | 1.0 |
| Deionized water | 87.8 |
| • 1-Tetradecanol | 1.5 |
| •• C-14 1EO (Tetradeceth-1) | 4.5 |
| + Octylacrylamide/acrylates copolymer | 1.5 |
| Propylene glycol | 2.5 |
| ++ Laurtrimonium chloride | 1.0 |
| | 100.0 |

* Ethoxylated $C_{9-11}$ alcohol of 6 mols of ethylene oxide per mol
** Cetyl trimethylammonium chloride
• Alfol ®14 alcohol (Vista Chemical Co.)
•• Alfonic ®14-17 ethoxylate (Vista Chemical Co., ethoxylated tetradecanol (C14), with an average degree of ethoxylation of one)
+ Versatyl ®42 (National Starch Corp., M.W. in range of 150,000 to 200,000)
++ Lauryl trimethylammonium chloride The rinse composition of this example is made in a similar manner as in EXAMPLE 1, except that the it is neutralized to 48% of the polymer capacity. The solvent used is a mixture of a $C_{10-14}$ alkanol and $C_{10-14}$ alcohol ethoxylate, having one ethoxy group per mole, in the ratio of approximately 1:3. The composition was tested by the same tests for conditioning and setting properties on human hair as in the previous examples. The ratings for conditioning and stiffness are set forth in Table I.

EXAMPLE 21

| Component | Percent (by weight) |
|---|---|
| * C9–11 Pareth-6 | 0.2 |
| ** Cetrimonium chloride | 1.0 |
| ▲ Protachem GMS 165 | 1.0 |
| Deionized water | 85.8 |
| 1-Tetradecanol | 4.0 |
| •• C-14 1EO (Tetradeceth-1) | 2.0 |
| + Octylacrylamide/acrylates copolymer | 1.5 |
| Propylene glycol | 2.5 |

-continued

| Component | Percent (by weight) |
|---|---|
| ++ Laurtrimonium chloride | 1.0 |
| ▲ Protachem GMS 165 | 1.0 |
| | 100.0 |

* Ethoxylated $C_{9-11}$ alcohol of 6 mols of ethylene oxide per mol
** Cetyl trimethylammonium chloride
▲ Protachem GMS 165 (Protameen Chemicals, Inc., glycerol monostearate and polyethylene stearate)
• Alfol ®14 alcohol (Vista Chemical Co.)
•• Alfonic ®14-17 ethoxylate (Vista Chemical Co., ethoxylated tetradecanol (C14), with an average degree of ethoxylation of one)
+ Versatyl ®42 (National Starch Corp., M.W. in range of 150,000 to 200,000)
++ Lauryl trimethylammonium chloride The rinse composition of this example is made in a similar manner as in EXAMPLE 1, except that the it is neutralized to 48% of the polymer capacity. The solvent used is a mixture of a $C_{10-14}$ alkanol and $C_{10-14}$ alcohol ethoxylate, having one ethoxy group per mole, in the ratio of approximately 2:1. The composition was tested by the same tests for conditioning and setting properties on human hair as in the previous examples. The ratings for conditioning and stiffness are set forth in Table I.

EXAMPLE 22

| Component | Percent (by weight) |
|---|---|
| * C9–11 Pareth-6 | 0.2 |
| ** Cetrimonium chloride | 1.0 |
| Deionized water | 86.55 |
| • 1-Tetradecanol | 3.0 |
| •• C-14 1EO (Tetradeceth-1) | 3.0 |
| ▲▲ Acrylamide/acrylate copolymer | 1.5 |
| Propylene glycol | 2.5 |
| ++ Laurtrimonium chloride | 1.0 |
| | 100.0 |

* Ethoxylated $C_{9-11}$ alcohol of 6 mols of ethylene oxide per mol
** Cetyl trimethylammonium chloride
• Alfol ®14 alcohol (Vista Chemical Co.)
•• Alfonic ®14-17 ethoxylate (Vista Chemical Co., ethoxylated tetradecanol (C14), with an average degree of ethoxylation of one)
▲▲ Ultrahold ®Strong (BASF, A.G., 10% carboxylic acid monomer)
++ Lauryl trimethylammonium chloride The rinse composition of this example is made in a similar manner as in EXAMPLE 1, except that the it is neutralized to 48% of the polymer capacity. The solvent used is a mixture of a $C_{10-14}$ alkanol and $C_{10-14}$ alcohol ethoxylate, having one ethoxy group per mole, in the ratio of approximately 1:1. The composition was tested by the same tests for conditioning and setting properties on human hair as in the previous examples. The ratings for conditioning and stiffness are set forth in Table I.

EXAMPLE 23

| Component | Percent (by weight) |
|---|---|
| * C9–11 Pareth-6 | 0.2 |
| ** Cetrimonium chloride | 1.0 |
| Deionized water | 88.8 |
| • 1-Tetradecanol | 4.0 |
| •• C-14 1EO (Tetradeceth-1) | 2.0 |
| + Octylacrylamid/acrylates copolymer | 1.5 |

| Component | Percent (by weight) |
|---|---|
| ++ Laurtrimonium chloride | 1.0 |
| Germaben II preservative | 0.5 |
| | 100.0 |

* Ethoxylated $C_{9-11}$ alcohol of 6 mols of ethylene oxide per mol
** Cetyl trimethylammonium chloride
• Alfol ®14 alcohol (Vista Chemical Co.)
•• Alfonic ®14-17 ethoxylate (Vista Chemical Co., ethoxylated tetradecanol (C14), with an average degree of ethoxylation of one)
+ Versatyl ®42 (National Starch Corp., M.W. in range of 150,000 to 200,000)
++ Lauryl trimethylammonium chloride The rinse composition of this example is made in a similar manner as the phase inversion technique in EXAMPLE 10. The polymer was neutralized to 5% capacity. The solvent used in this example is a mixture of a $C_{10-14}$ alkanol and $C_{10-14}$ alcohol ethoxylate, having one ethoxy group per mole, in the ratio of approximately 2:1. The composition was tested by the same tests for conditioning and setting properties on human hair as in the previous examples. The ratings for conditioning and stiffness are set forth in Table L

EXAMPLE 24

| Component | Percent (by weight) |
|---|---|
| * C9–11 Pareth-6 | 0.2 |
| ** Cetrimonium chloride | 1.0 |
| Deionized water | 83.3 |
| ♦♦ C-16 ½EO | 6.0 |
| + Octylacrylamide/acrylates copolymer | 1.5 |
| Propylene glycol | 2.5 |
| ++ Laurtrimonium chloride | 1.0 |
| Germaben II preservative | 0.5 |
| | 100.0 |

* Ethoxylated $C_{9-11}$ alcohol of 6 mols of ethylene oxide per mol
** Cetyl trimethylammonium chloride
• Alfol ®14 alcohol (Vista Chemical Co.)
♦♦ Alfonic ®16-8 ethoxylate (Vista Chemical Co., ethoxylated NAME hexadecanol (C16), with an average degree of ethoxylation of ½)
+ Versatyl ®42 (National Starch Corp., M.W. in range of 150,000 to 200,000)
++ Lauryl trimethylammonium chloride The rinse composition of this example is made in a similar manner as in EXAMPLE 1, except that it is neutralized to 5% of the polymer capacity. The solvent used is a $C_{10-20}$ alcohol ethoxylate, having ½ ethoxy group per mole. The composition was tested by the same tests for conditioning and setting properties on human hair as in the previous examples. The ratings for conditioning and stiffness are set forth in Table L

EXAMPLE 25

| Component | Percent (by weight) |
|---|---|
| * C9–11 Pareth-6 | 0.2 |
| ** Cetrimonium chloride | 1.0 |
| Deionized water | 86.3 |
| Propylene Glycol | 2.5 |
| • 1-Tetradecanol | 4.0 |
| •• C-14 1EO (Tetradeceth-1) | 2.0 |
| + Octylacrylamide/acrylates copolymer | 1.5 |

| Component | Percent (by weight) |
|---|---|
| ++ Laurtrimonium chloride | 1.0 |
| Germaben II preservative | 0.5 |
| | 100.0 |

* Ethoxylated $C_{9-11}$ alcohol of 6 mols of ethylene oxide per mol
** Cetyl trimethylammonium chloride
• Alfol ®14 alcohol (Vista Chemical Co.)
•• Alfonic ®14-17 ethoxylate (Vista Chemical Co., ethoxylated tetradecanol (C14), with an average degree of ethoxylation of one)
+ Versatyl ®42 (National Starch Corp., M.W. in range of 150,000 to 200,000)
++ Lauryl trimethylammonium chloride The rinse composition of this example is made in a similar manner as in EXAMPLE 1, except that it is neutralized to 5% of the polymer capacity. The solvent used is a mixture of a $C_{10-14}$ alkanol and $C_{10-14}$ alcohol ethoxylate, having one ethoxy group per mole, in the ratio of approximately 2:1. The composition was tested by the same tests for conditioning and setting properties on human hair as in the previous examples. The ratings for conditioning and stiffness are set forth in Table L

EXAMPLE 26

| Component | Percent (by weight) |
|---|---|
| * C9–11 Pareth-6 | 0.2 |
| ** Cetrimonium chloride | 1.0 |
| Deionized water | 86.3 |
| Propylene Glycol | 2.5 |
| • 1-Tetradecanol | 4.0 |
| •• C-14 1EO (Tetradeceth-1) | 2.0 |
| + Octylacrylamide/acrylates copolymer | 1.5 |
| ++ Laurtrimonium chloride | 1.0 |
| Germaben II preservative | 0.5 |
| | 100.0 |

* Ethoxylated $C_{9-11}$ alcohol of 6 mols of ethylene oxide per mol
** Cetyl trimethylammonium chloride
• Alfol ®14 alcohol (Vista Chemical Co.)
•• Alfonic ®14-17 ethoxylate (Vista Chemical Co., ethoxylated tetradecanol (C14), with an average degree of ethoxylation of one)
+ Versatyl ®42 (National Starch Corp., M.W. in range of 150,000 to 200,000)
++ Lauryl trimethylammonium chloride The rinse composition of this example is made in a similar manner as in EXAMPLE 1, except that it is neutralized to 48% of the polymer capacity. The solvent used is a mixture of a $C_{10-14}$ alkanol and $C_{10-14}$ alcohol ethoxylate, having one ethoxy group per mole, in the ratio of approximately 2:1. The composition was tested by the same tests for conditioning and setting properties on human hair as in the previous examples. The ratings for conditioning and stiffness are set forth in Table L

TABLE I

SUMMARY OF CONDITIONING AND SETTING PROPERTIES OF EXAMPLES 11 TO 26

| EXAMPLE | COMBING | STIFFNESS |
|---|---|---|
| 11 | 3.25 slight drag | 3.5 stiff |
| 12 | 3.50 easy combing | 3.25 fairly stiff |
| 13 | 4.0 easy combing | 3.5 stiff |
| 14 | 3.5 easy combing | 4.0 stiff |
| 15 | 3.5 easy combing | 3.25 rubbery stiff |

TABLE I-continued

SUMMARY OF CONDITIONING AND SETTING PROPERTIES OF EXAMPLES 11 TO 26

| EXAMPLE | COMBING | STIFFNESS |
| --- | --- | --- |
| 16 | 3.5 easy combing | 3.75 stiff |
| 17 | 3.5 easy combing | 3.5 rubbery stiff |
| 18 | 3.75 easy combing | 3.25 fairly stiff |
| 19 | 3.25 fairly easy | 3.5 rubbery stiff |
| 20 | 3.25 fairly easy | 3.75 stiff |
| 21 | 3.0 some snag | 2.75 light hold |
| 22 | 3.25 fairly easy | 3.25 fairly stiff |
| 23 | 4.25 very smooth | 4.0 stiff |
| 24 | 3.25 slight drag | 3.75 stiff |
| 25 | 2.75 snags | 2.25 light |
| 26 | 4.25 very smooth | 3.25–3.50 stiff |

The results in Table I summarizing the properties of Examples 11 to 26 illustrate that compositions using solvents comprised of $C_{10-14}$ alcohols or $C_{14-20}$ alcohol ethoxylates having less than 2 ethoxy groups per mole or mixtures of $C_{10-14}$ alcohols and $C_{14-20}$ alcohol ethoxylates having less than 2 ethoxy groups per mole, in the ratio ranging from 2:1 to 1:3 provide desirable conditioning and setting properties.

In all the compositions of the working examples, as illustrated in the formulas presented, the dispersion or emulsion made is a useful one-step rinse for imparting to the hair both conditioning and ease-of-setting properties. Examples 1-10, 12, 21 and 23-25 are the most stable composition formulations. All the rinses of the examples are in attractive thick lotion form, with viscosities in the range of 1,000 to 5,000 centipoises and pH's in the range of 3–7. In all the examples the invented rinse composition is applied to shampooed hair but it is considered that the compositions are also applicable to hair that has not been shampooed immediately beforehand and that similar results will be obtained.

The various advantages and unique features of the present invention have been mentioned previously but will be briefly summarized here, too. First and foremost, a one-step rinse application results in both conditioning of the hair and increasing the body thereof. Why such desirable results are obtained is not known for sure, and the observed results seem improbable from the art, especially in light of the negative electrical charge of the polymer, which would be expected to cause it to be repelled by the hair from relatively dilute aqueous media. On the contrary, when the present compositions are used the polymer deposits on the hair and stiffness it. Whether the quat and the polymer form a complex and, if they do, what the part of the solvent is in such formation has not been established for certain yet. Why certain solvent compositions are more effective than others in promoting improved conditioning (and bodying) by the invented compositions is not known. What is known is that when the types and proportions of the quat, polymer and solvent are properly balanced one is able to obtain conditioning and bodying from a single rinse, despite the fact that such properties have often been considered to be opposed to each other and even incompatible.

The invention has been described with respect to illustrations and examples thereof but is not to be limited to those because it is considered that one of skill in the art will be able to utilize substitutes and equivalents to make such compositions without departing from the scope and spirit of the invention as defined in the claims appended hereto.

We claim:

1. A process for manufacturing a hair rinse composition in oil-in-water or dispersion form comprising:

making separate water and oil phase mixtures;

heating both phases to a temperature in the range of 75° to 90° C.;

adding the heated oil phase to the heated water phase to form an oil-in-water emulsion;

said emulsion manufactured comprises 1 to 4% of $C_{10-18}$ alkyl trimethyl ammonium chloride, 1 to 4% of an acrylamide acrylate copolymer, 3 to 8% of a $C_{9-20}$ alkanol and/or $C_{9-20}$ alcohol ethoxylate having less than 2 ethoxy groups per mole, 1 to 5% of propylene glycol, 0.1 to 0.5% of a nonionic surfactant or a mixture of such surfactant with anionic surfactant, and water, wherein said water phase is a mixture of the surfactant(s), about half of the quaternary ammonium salt, and water, and said oil phase is a mixture of the acrylamide acrylate copolymer, $C_{9-20}$ alkanol and/or $C_{9-20}$ alcohol ethoxylate having less than 2 ethoxy groups per mole, the propylene glycol, and about half of the quaternary ammonium salt.

2. A process according to claim 1 wherein the emulsion formed is treated with an alkaline material to partially neutralize the polymer.

3. A process according to claim 2 wherein the emulsion formed is treated with an aqueous solution of KOH during the cooling of the emulsion to neutralize the copolymer to the extent of 5 to 100%.

* * * * *